United States Patent [19]

Coss et al.

[11] Patent Number: 5,733,117
[45] Date of Patent: Mar. 31, 1998

[54] STERILE FLUID DELIVERY SYSTEM AND METHOD

[75] Inventors: Ronald G. Coss, Newport Beach; Jay R. McCoy, Trabuco Canyon, both of Calif.

[73] Assignee: Micro Motors, Inc., Santa Ana, Calif.

[21] Appl. No.: 539,936

[22] Filed: Oct. 6, 1995

[51] Int. Cl.$^6$ ................................................. A61C 1/10
[52] U.S. Cl. ........................... 433/85; 433/82; 433/126
[58] Field of Search ........................ 433/80, 81, 82 R, 433/84, 85 R, 86, 98, 126 R; 601/162, 163, 164, 165

[56] References Cited

U.S. PATENT DOCUMENTS

| | | | |
|---|---|---|---|
| 3,106,021 | 10/1963 | Bordon | 433/80 |
| 4,113,627 | 9/1978 | Leason | 264/251 |
| 4,193,196 | 3/1980 | Kuris et al. | 433/82 |
| 4,201,200 | 5/1980 | Hubner | 601/162 |
| 4,276,023 | 6/1981 | Phillips et al. | 433/85 |
| 4,302,185 | 11/1981 | Hall | 433/84 |
| 4,359,317 | 11/1982 | Strohmaier et al. | 433/85 |
| 4,470,812 | 9/1984 | Martens et al. | 433/85 |
| 4,505,676 | 3/1985 | Gonser | 433/86 |
| 4,973,247 | 11/1990 | Varnes et al. | 433/85 |
| 5,019,038 | 5/1991 | Linden | 604/49 |
| 5,125,837 | 6/1992 | Warrin et al. | 433/86 |
| 5,156,546 | 10/1992 | Frank et al. | 433/25 |
| 5,204,004 | 4/1993 | Johnston et al. | 433/80 |
| 5,261,816 | 11/1993 | Varnes | 433/84 |
| 5,295,829 | 3/1994 | Frey et al. | 433/82 |
| 5,360,338 | 11/1994 | Waggoner | 433/80 |
| 5,511,977 | 4/1996 | Futch, Jr. | 433/126 |

OTHER PUBLICATIONS

SteriWater Sterile Water Delivery System advertising brochure.
Clearline Microfiltration Cartridge advertising brochure.
Forest Sterile Water System Data Sheet.
Article on handpiece coolant.

*Primary Examiner*—John J. Wilson
*Attorney, Agent, or Firm*—Knobbe, Martens Olson & Bear, LLP

[57] ABSTRACT

A sterile fluid delivery system that incorporates a specialized handpiece adapter placed between a standard dental or other medical handpiece and a conventional tube set. The tap water conduit in the conventional tube set is blocked by the handpiece adapter and instead a tube set connected to the adapter provides a supply of sterile fluid for delivery to a work site. A peristaltic pump delivers fluid from a sterile supply to the handpiece adapter. Motor exhaust air pressure from the adapter is applied to the pump to activate a pressure-sensitive switch. The pump automatically turns on when the medical tool is activated and turns off when the tool is deactivated.

26 Claims, 4 Drawing Sheets

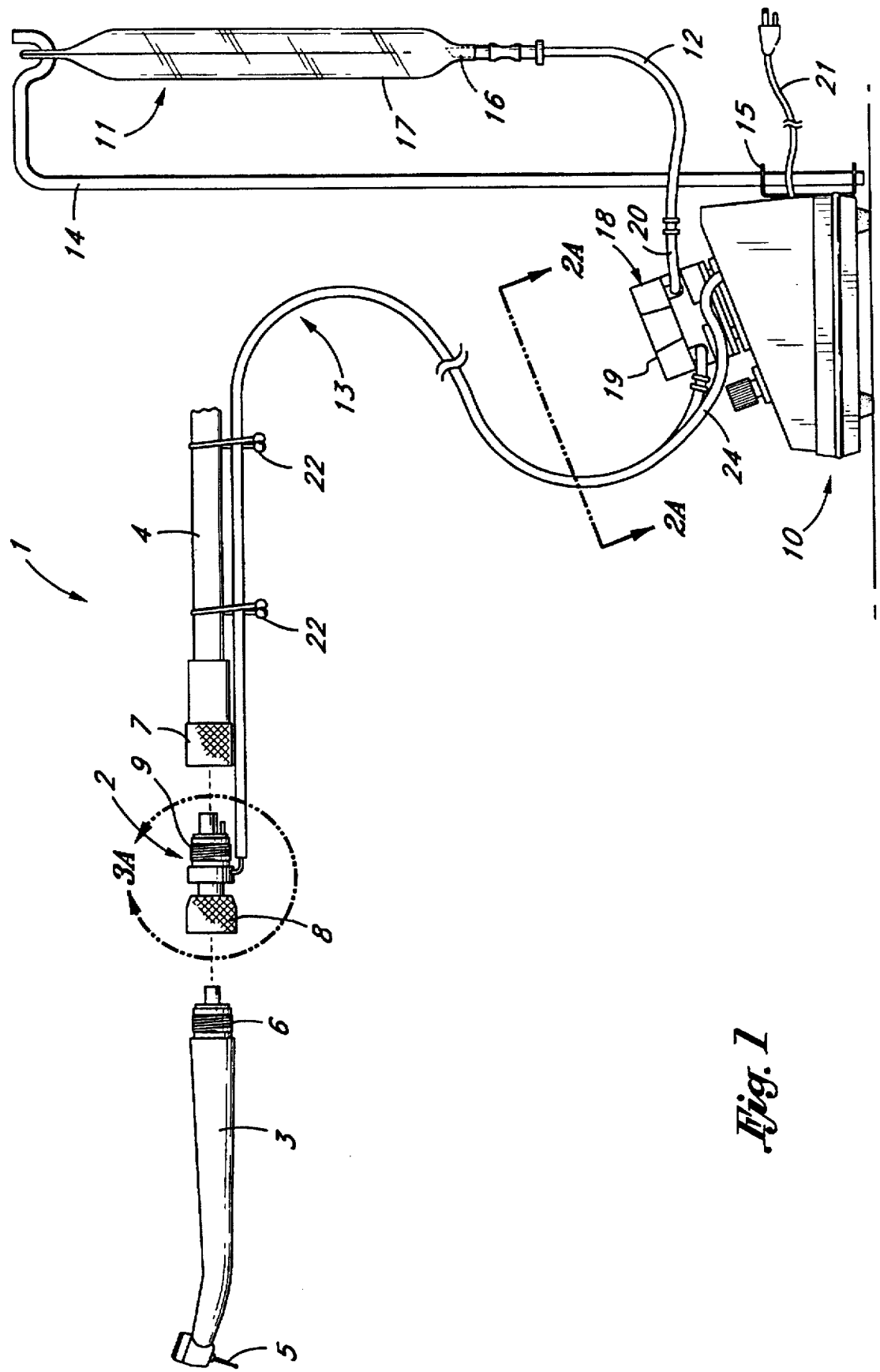

STERILE FLUID DELIVERY SYSTEM AND METHOD

FIELD OF THE INVENTION

This invention is in the field of delivering sterile water or other fluid to medical air-powered instruments, more commonly dental handpieces.

BACKGROUND OF THE INVENTION

Many of the powered tools employed by modern dentists and oral surgeons operate by means of an air-driven motor. In operation, a stream of high-pressure air from an inlet conduit rotates the motor and exits through an exhaust conduit. The rotating motor in turn rotates a rotatably connected tool, such as a drill.

Because of the heat generated by the friction between the rotating tool and the patient's hard tissue (e.g., bone or teeth), it is necessary to supply a stream of coolant water to the work site. In addition to performing a cooling function, the water is also useful for irrigating the work site, removing the debris created during the tool's operation.

The tool is mounted on one end of a standard dental or surgical handpiece, which in turn connects to a conventional tube set, which is usually part of a conventional dental or surgical unit. This tube set provides conduits for inlet air to drive the motor and exhaust air from the motor. The conventional tube set also contains a conduit for the cooling and irrigating water, and may further contain a conduit for the chip air. A separate conduit for a fiber optic cable may also be contained in the conventional tube set.

Conventional dental units have traditionally used water from a community source, often called "tap water". Tap water contamination and water line contamination within the dental unit have led to concerns over patient safety. This has led to the development of a number of systems that use water from a sterile water source. One such system is disclosed in U.S. Pat. No. 4,470,812 to Martens, et al., in which a disposable dual chamber cartridge of sterile water is interposed in the normal tap water delivery line. Pressure from the tap water flows into a first cartridge chamber and forces sterile water from a second adjacent cartridge chamber into the dental handpiece for delivery to the work site. One drawback of this system is the potential for the tap water to contaminate the sterile water in the event the seal separating the two chambers loses its integrity. Furthermore, continuously filling the cartridge with tap water during operation of the dental tool requires vigilance to ensure that the cartridge does not overfill and potentially burst. While the use of a short sterile water supply tube permits the cartridge to be located near the dental handpiece, this arrangement is inconvenient for the operator and may also interfere with the operation of the handpiece. Moreover, disposal of the sterile water cartridge after only a single use can be somewhat costly.

Another system is disclosed in U.S. Pat. No. 5,360,338 to Waggoner, in which a dental handpiece is connected to a control box containing internal air and sterile water supply networks. A drawback of this system is its complex arrangement of tubing, connectors, and valves to provide sterile water during the operation of the dental tool.

It is therefore highly desirable to provide a simple sterile fluid supply system that connects to both a standard dental handpiece and a conventional tube set and eliminates the risks of fluid contamination and system overfilling.

SUMMARY OF THE INVENTION

The present invention provides a sterile fluid delivery system that incorporates a specialized handpiece adapter placed between a standard medical handpiece and a conventional tube set. An adapter tube set is connected to the handpiece adapter and provides a supply of sterile fluid to the handpiece for delivery to the work site. As with the medical handpiece and medical tools, the handpiece adapter and its associated tube set can be removed and sterilized. This sterilization prevents any contaminated fluid from remaining in the handpiece, the adapter, or the adapter tube set after it has been used for treating any given patient.

In the preferred embodiment of the invention, a peristaltic pump delivers water from a sterile water supply to the handpiece adapter. Air pressure which is provided to operate a motor or other tool connected to the handpiece is utilized to initiate operation of the pump. Preferably, motor exhaust air from the adapter is delivered to the pump to activate a pressure-sensitive switch. In the preferred mode of operation, then, the pump automatically turns on when the dental tool is activated and turns off when the tool is deactivated. The operator of the dental tool thus need not be concerned about any controls to initiate the delivery of the sterile water. Further, in this embodiment, the tap water conduit in the conventional tube set is blocked by the handpiece adapter. Consequently, the tap water supply should be turned off altogether.

In a second embodiment of the invention, tap water is delivered from the handpiece adapter to a small, disposable external water filter. The tap water passes through the filter and is, in turn, delivered back to the handpiece adapter. In this embodiment, there is no possibility that the tap water can contaminate the filtered water. In addition, the light weight filter can be easily carried adjacent to the adapter, and frequent replacement of the filter is easy and practical.

BRIEF DESCRIPTION OF THE DRAWINGS

FIG. 1 is a side elevational view of the sterile water delivery system.

DETAILED DESCRIPTION

Figure 2A:
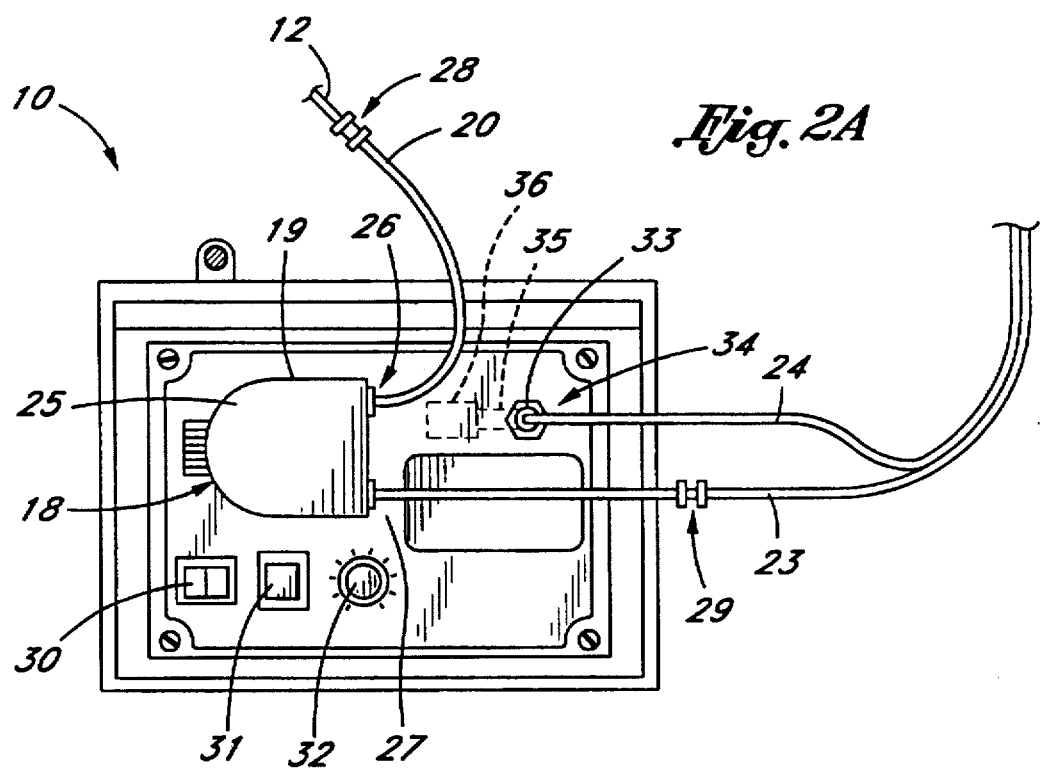
FIG. 2A is a top plan view of the pump unit with the pump housing cover closed and all of the tubes connected.

Referring now to the drawings, FIG. 1 shows an overview of the preferred embodiment of the sterile water delivery system 1. The system 1 includes a handpiece adapter 2, which is interposed between a standard handpiece 3 and a conventional tube set 4. The handpiece 3 has a tool 5 located at its forward end and connecting threads 6 at its rearward end. The conventional tube set 4 has a connector 7 at its forward end and is connected to one or more air supplies and a community water supply at its rearward end (not illustrated). In a conventional system, the connector 7 of the conventional tube set 4 is connected to the standard handpiece 3 via its connecting threads 6.

The handpiece adapter 2 has a generally cylindrically shaped body with a connector 8 at its forward end that is substantially identical to the connector 7 of the conventional tube set 4. The handpiece adapter 2 also has connecting threads 9 at its rearward end that are substantially identical to the connecting threads 6 of the handpiece 3. As a result, the handpiece adapter 2 can be connected directly in line between the conventional tube set 4 and the standard handpiece 3.

Figure 2B:
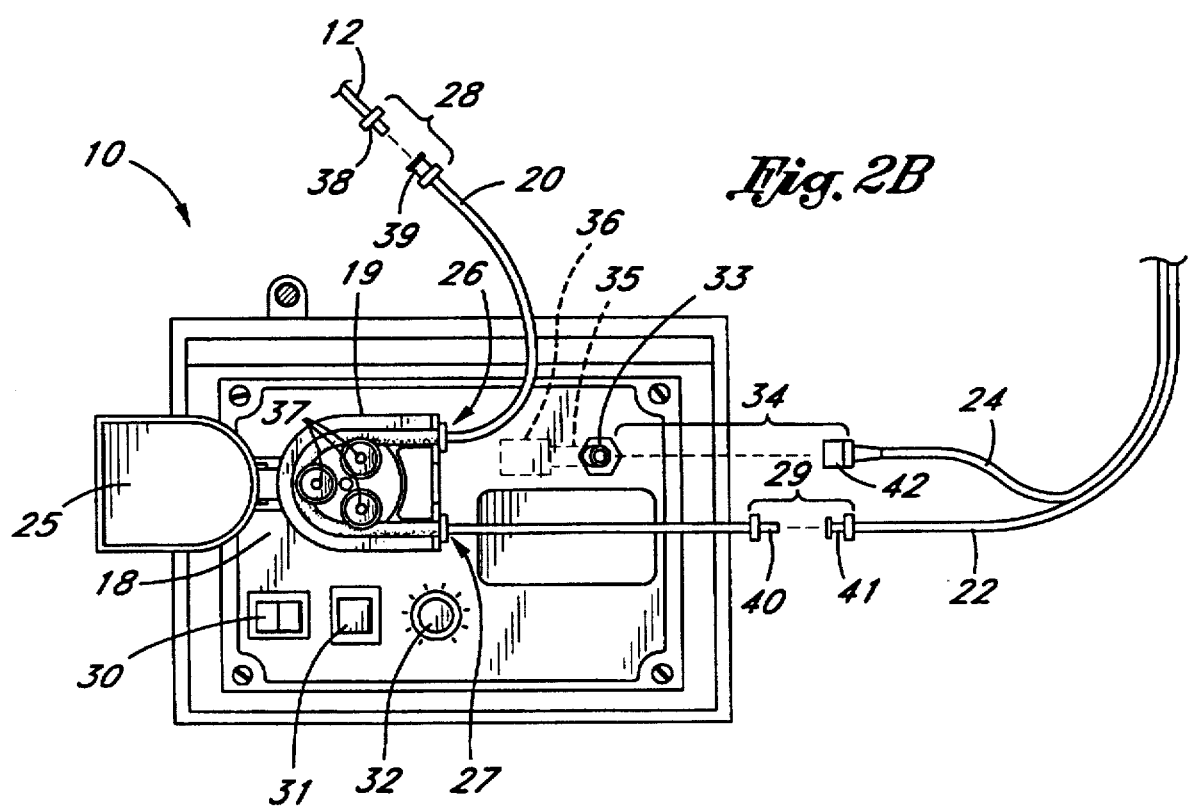
FIG. 2B is a plan view of the pump unit with the pump housing cover open and all of the tubes disconnected.

Referring to FIGS. 2A and 2B as well as FIG. 1, the sterile water delivery system 1 also includes a pump unit 10 and a sterile water supply 11. A supply tube 12 connects the sterile water supply 11 to the pump unit 10 and an adapter tube set 13 connects the pump unit 10 to the handpiece adapter 2. The sterile water supply 11 is hung from a water supply hanger 14, which is mounted at the rear of the pump unit 10 via hanger mounting bracket 15. The sterile water supply may also be provided by a bottle of sterile water (not illustrated). The supply tube 12 has a spike 16 at its rearward end that punctures the sterile water supply 11, allowing sterile water 17 to flow from the sterile water supply 11 to the pump unit 10.

The pump unit 10 preferably includes a peristaltic pump 18 and has a pump housing 19 on its upper surface. Peristaltic pumps are well known in the art, such as Micro Motors, Inc.'s Micro SWP Sterile Water Pump or Omega Engineering, Inc.'s "OMEGAFLEX"® Peristaltic Pump. One advantage of using a peristaltic pump is that the pumping chamber consists of a fluid tube or "pump tube" 20. The sterile water 17 is confined within the pump tube 20 and is thus not contaminated by the peristaltic pump 18. Other advantages include positive displacement of the sterile water 17, no back flow of the sterile water 17, self-priming of the pump 18, siphoning of the sterile water 17 is not necessary, and the peristaltic pump 18 can run with no sterile water 17 in the pump tube 20 without damage.

The pump tube 20 runs through the pump housing 19 on the pump unit 10. The rearward end of the pump tube 20 connects to the forward end of the supply tube 12, thereby allowing the pump tube 12 to receive sterile water 17 from sterile water supply 11. In addition, a power cord 21 is attached to the rear of pump unit 10 and plugs into an electrical outlet (not illustrated) to provide power to the pump unit 10.

The adapter tube set 13, preferably mounted alongside the conventional tube set 4 via twist type clips 22, comprises both an irrigation tube 23 and a control signal tube 24. The rearward end of the irrigation tube 23 is connected to the forward end of the pump tube 20, and the forward end of the irrigation tube 23 is connected to the handpiece adapter 2. This arrangement allows sterile water 17 to be delivered to the handpiece adapter 2 from the pump tube 20 via the irrigation tube 23.

In addition, the rearward end of the control signal tube 24 is connected to the pump unit 10, and the forward end of the control signal tube 24 is connected to the handpiece adapter 2. In the preferred mode of operation, when the tool 5 on the standard handpiece 3 is in operation, the control signal tube 24 provides the pump unit 10 with a signal to turn the pump unit 10 on.

FIG. 2A shows a first detailed view of the pump unit 10. In this view, a pump housing cover 25 is in its closed position and each of the tube connections has been made. More particularly, pump tube 20 enters an input side 26 of the peristaltic pump 18 and exits an output side 27 of the peristaltic pump 18. The pump tube 20 connects to the supply tube 12 at a first fluid connection 28 and to the irrigation tube 23 at a second fluid connection 29.

The pump unit 10 also includes a power switch 30, a switch selector 31, a flow rate adjuster 32, and a control signal fitting 33. The switch selector 31 allows the operator to choose among two modes of operation of the pump unit 10, automatic mode (operates when the handpiece is on) or manual mode. The flow rate adjuster 32 allows the operator to adjust the rate of flow of the sterile water 17 through the pump tube 20. Finally, at a control signal connection 34, the control signal fitting 33 is connected to the control signal tube 24 on its upper side and a short pressure-sensitive switch tube 35 on its lower side. The pressure-sensitive switch tube 35 is, in turn, connected to a pressure-sensitive switch 36 located inside the pump unit 10. The preferred pressure-sensitive switch 36 is manufactured by Press-Air-Trol of New York. The pressure-sensitive switch 36 responds to a control signal from the control signal tube 24, turning the pump unit 10 "on" when the tool 5 has been activated and "off" when the tool 5 has been deactivated.

FIG. 2B shows a second detailed view of the pump unit 10. In this view, the pump housing cover 25 is in its open position and each of the tube connections have been undone. More particularly, the peristaltic pump 18 contains three pump rollers 37. The pump tube 20 passes between the pump rollers 37 and the pump housing 19.

The first fluid connection 28 comprises a male luer 38 on the forward end of the supply tube 12 and a female luer 39 on the rearward end of the pump tube 20. The male luer 38 is inserted in its counterpart female luer 39 to permit sterile water 17 to pass from the supply tube 12 into the pump tube 20.

Similarly, the second fluid connection 29 comprises a male luer 40 on the forward end of the pump tube 20 and a female luer 41 on the rearward end of the irrigation tube 23. Again, the male luer 40 is inserted in its counterpart female luer 41 to permit sterile water 17 to pass from the pump tube 20 into the irrigation tube 23.

Finally, the control signal connection 34 comprises the control signal fitting 33 on the pump unit 10 and a tube fitting 42 on the rearward end of the control signal tube 24. The tube fitting 42 is inserted onto the control signal fitting 33 to permit the control signal to pass from the control signal tube 24, through the control signal fitting 33 and pressure-activated switch tube 35, and to the pressure-activated switch 36 inside the pump unit 10.

FIGS. 3A–3D show detailed views of the preferred embodiment of the handpiece adapter 2. The handpiece adapter 2 comprises an adapter body 43 with a connector 8 on its forward end and connecting threads 9 on its rearward end. Four separate conduits pass longitudinally through the entire length of the handpiece adapter 2: (1) an inlet air conduit 4; (2) an exhaust air conduit 45; (3) a chip air conduit 46; and (4) a fiber optic conduit 47. In addition, a water conduit 48 passes longitudinally through the forward portion of the handpiece adapter 2.

An inlet air tube 49 extends from the rear of the handpiece adapter 2 and connects to the inlet air conduit 44 and a corresponding conduit (not illustrated) in the conventional tube set 4. Similarly, an exhaust air tube 50 extends from the rear of the handpiece adapter 2 and connects to the exhaust air conduit 45 and a corresponding conduit (not illustrated) in the conventional tube set 4. Further, a chip air tube 51 extends from the rear of the handpiece adapter 2 and connects to the chip air conduit 46 and a corresponding conduit (not illustrated) in the conventional tube set 4. Finally, the fiber optic conduit 47 aligns with a corresponding conduit (not illustrated) in the conventional tube set 4.

Figure 3A:
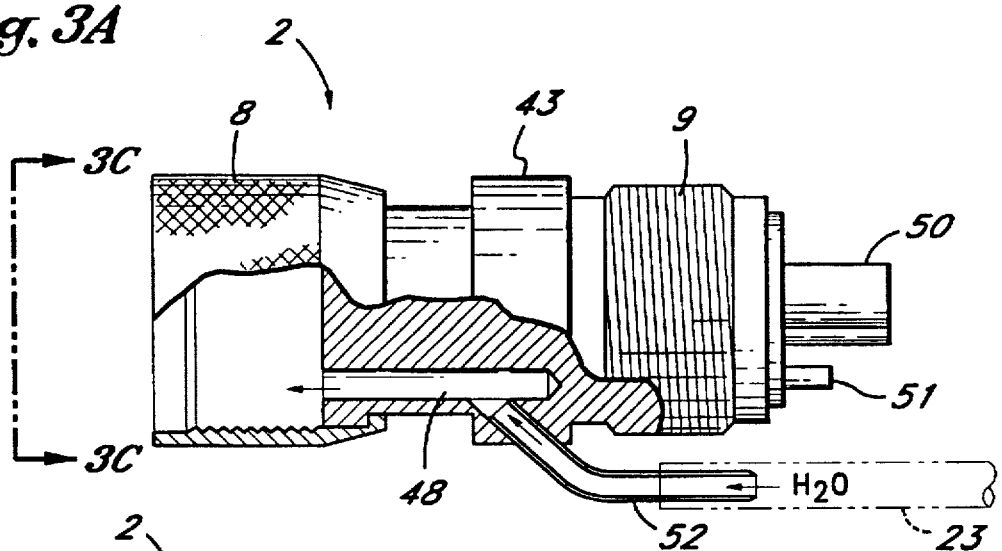
FIG. 3A is a left side elevational view of the preferred embodiment of the handpiece adapter with a cut-away sectional view of the water tube-in and conduit.
Figure 3B:
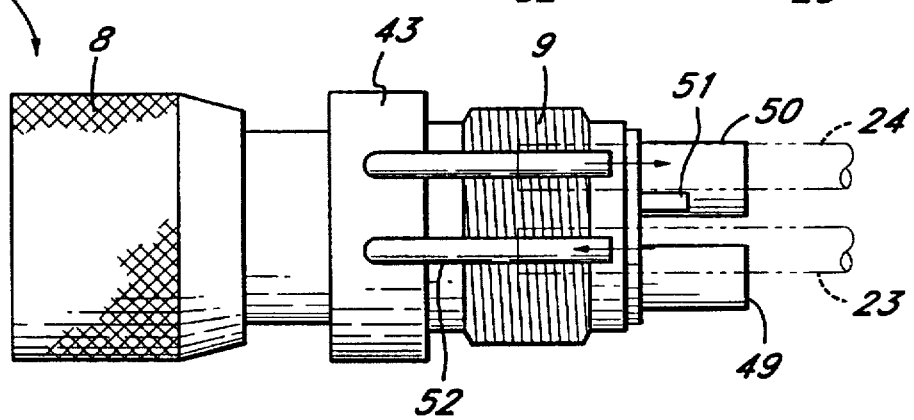
FIG. 3B is a bottom plan view of the preferred embodiment of the handpiece adapter.
Figure 3C:
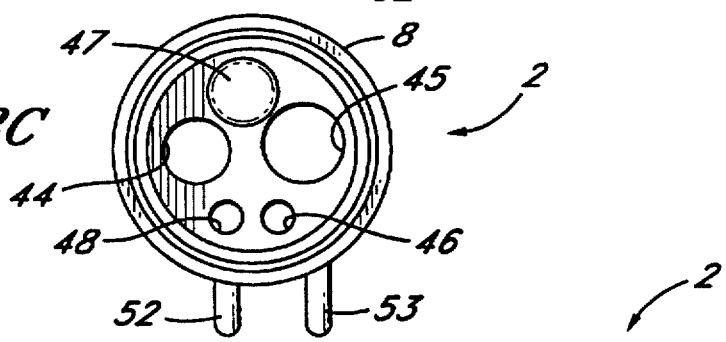
FIG. 3C is a forward end elevational view of the preferred embodiment of the handpiece adapter.

As illustrated in FIG. 3A, an important aspect of the preferred embodiment of the invention is that the water conduit 48 does not pass through the entire length of the handpiece adapter 2. Instead, the water conduit 48 passes through the forward portion of the handpiece adapter 2 and through the outer side surface of the adapter body 43, where a water tube-in 52 is rigidly inserted into the water conduit 48. The water tube-in 52 extends below the adapter body 43 and projects rearwardly, positioned such that it will not interfere with the connector 7 of the conventional tube set 4 and the connecting threads 9 of the handpiece adapter 2.

The forward end of the irrigation tube 23 is connected to the water tube-in 52 to supply sterile water 17 to the handpiece adapter 2. With this configuration, no tap water is supplied by the conventional tube set 4, and indeed the handpiece adapter 2 blocks off the tap water conduit in the conventional tube set 4. Thus, tap water cannot be inadvertently supplied to contaminate the sterile water 17. Consequently, when using the preferred embodiment of the invention, the tap water supplied to the conventional tube set 4 should be turned off at its source.

Figure 3D:
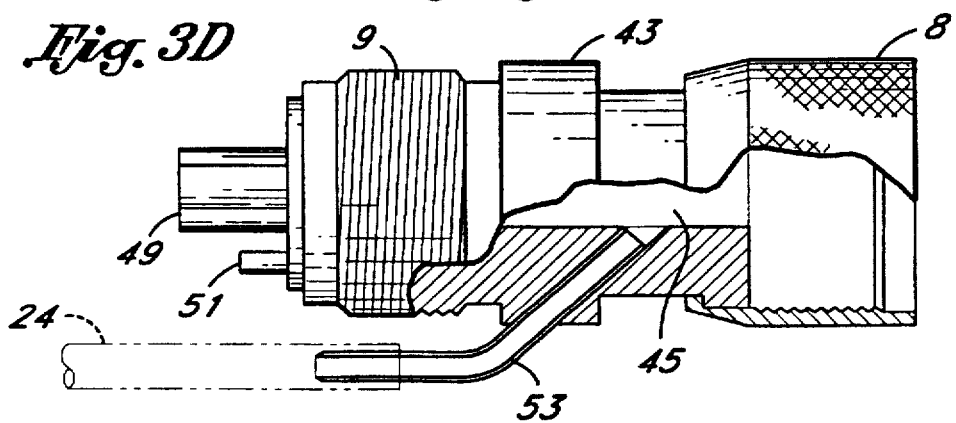
FIG. 3D is a right side elevational view of the preferred embodiment of the handpiece adapter with a cut-away sectional view of the exhaust air tube-out and conduit.

A further important aspect of the preferred embodiment of the invention is illustrated in FIG. 3D. The high-pressure air from the inlet air conduit 44 is typically delivered to the air-driven motor, subsequently passing through the exhaust air conduit 45 at a considerably lower pressure (depending on the outlet conditions). The exhaust air conduit 45 not only passes longitudinally through the entire length of the handpiece adapter 2 but also branches off through the outer side surface of the adapter body 43, where an exhaust air tube-out 53 is rigidly inserted into the exhaust air conduit 45. As with the water tube-in 52, the exhaust air tube-out 53 extends below the adapter body 43 and projects rearwardly, positioned such that it will not interfere with the connector 7 of the conventional tube set 4 and the connecting threads 9 of the handpiece adapter 2.

The forward end of the control signal tube 24 is connected to the exhaust air tube-out 53 to permit a portion of the exhaust air to be diverted from the exhaust air conduit 45 to the control signal tube 24. With this configuration, when the dental tool 5 is activated, the pressure of the exhaust air returning from the air-driven motor is applied through the control signal tube 24 to be sensed by the pressure-sensitive switch 36 in the pump unit 10. The pressure-sensitive switch 36, sensing the increased pressure in the control signal tube 24, turns on the peristaltic pump 18, thereby commencing delivery of the sterile water 17 through the irrigation tube 23 to the handpiece adapter 2. Correspondingly, when the dental tool 5 is deactivated, the peristaltic pump 18 is automatically turned off by the pressure sensitive switch 36, thereby ceasing delivery of the sterile water 17 to the handpiece adapter 2. The pressure-sensitive switch 36 preferably responds to an air pressure of approximately 0.5 pounds per square inch.

Although utilizing exhaust air pressure to activate the pump is preferred, because the fluid flow stops as soon as air flow to the air motor stops, it should be recognized that inlet air could be ducted to the pressure responsive switch. It has been found, however, that, the inlet pressure may keep the fluid delivery pump running for a few seconds after the air motor stops. Thus fluid continues to be provided to the tool site when none is needed.

A primary advantage of the present invention is the ability to sterilize each of the components that may become contaminated during operation of the system 1. Not only can the dental tool 5 and the standard handpiece 3 be sterilized, but the handpiece adapter 2, the adapter tube set 13, and the pump tube 20 can also be sterilized after each use. Each of these components can, for example, be disassembled from each other and placed in an autoclave after the components have been used with a given patient. After any contamination has been eliminated, the components can be reassembled for use with the next patient.

Figure 4A:
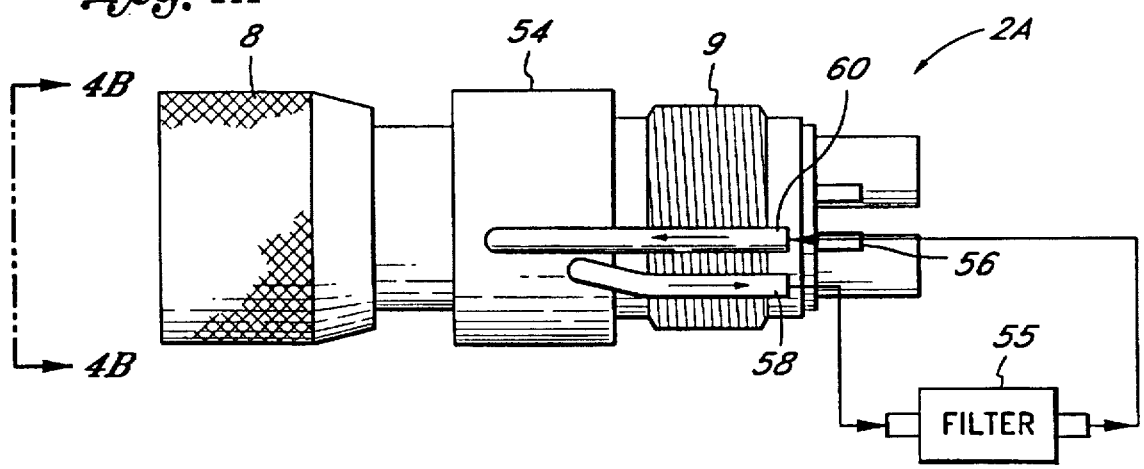
FIG. 4A is a bottom plan view of a second embodiment of the handpiece adapter.
Figure 4B:
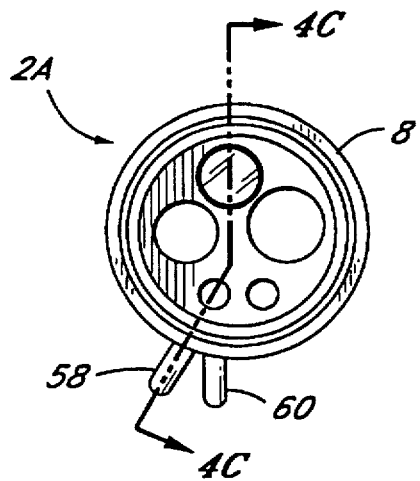
FIG. 4B is a forward end elevational view of the second embodiment of the handpiece adapter.
Figure 4C:
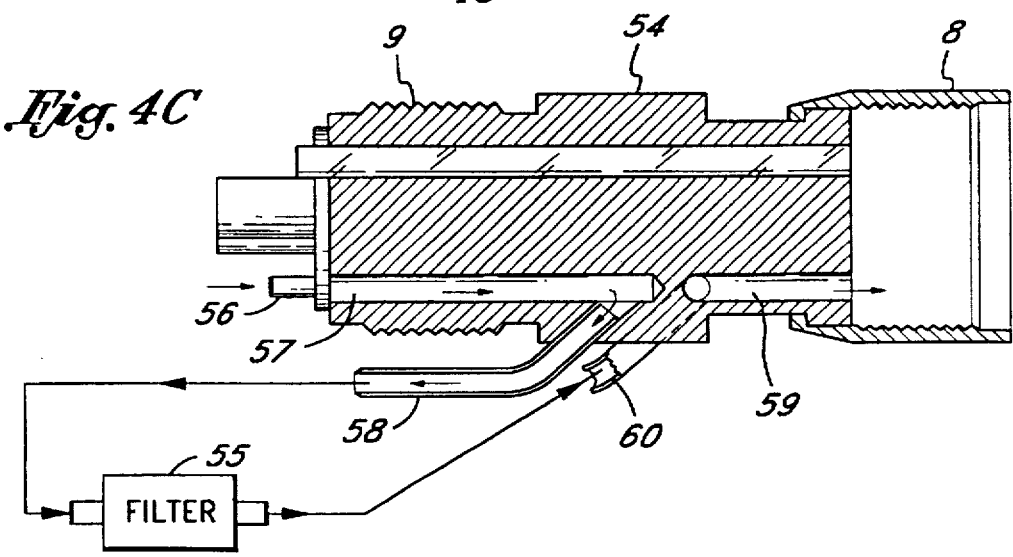
FIG. 4C is a right side elevational view of the second embodiment of the handpiece adapter with a cut-away sectional view of the water tube-in, tube-out, and conduits.

FIGS. 4A–4C show detailed views of a second embodiment of the handpiece adapter 2A. The handpiece adapter 2A comprises an adapter body 54 with a connector 8 on its forward end and connecting threads 9 on its rearward end. The handpiece adapter 2A of the second embodiment differs from the preferred embodiment in that it uses tap water supplied from the conventional tube set 4, passes that tap water through a suitable external water filter 55, and returns the filtered water to the handpiece adapter 2A for delivery to the work site. The particular filter used does not form a part of the present invention. SciTech Dental, Inc. of Seattle, Wash. markets a filter identified as "CLEARLINE"™ Microfiltration Cartridge, under U.S. Pat. Nos. 4,113,627 and 5,204,004. SciTech indicates such filter is suitable for use with the adapter 2A. As illustrated in FIGS. 4A–4C, the second embodiment does not have an exhaust air tube-out.

In this embodiment, a tap water tube 56 extends from the rear of the handpiece adapter 2A and connects to a tap water conduit 57 in the handpiece adapter 2A and a corresponding conduit (not illustrated) in the conventional tube set 4. The tap water conduit 57 passes through the rearward portion of the handpiece adapter 2A and through the outer side surface of the adapter body 54, where a tap water tube-out 58 is rigidly inserted into the tap water conduit 57. The tap water tube-out 58 extends below the adapter body 54 and projects rearwardly, positioned such that it will not interfere with the connector 7 of the conventional tube set 4 and the connecting threads 9 of the handpiece adapter 2A.

Similar to the preferred embodiment, a filtered water conduit 59 passes through the forward portion of the handpiece adapter 2A and through the outer side surface of the adapter body 54, where a filtered water tube-in 60 is rigidly inserted into the filtered water conduit 59. The filtered water tube-in 60 extends below the adapter body 54 and projects rearwardly, positioned such that it will not interfere with the connector 7 of the conventional tube set 4 and the connecting threads 9 of the handpiece adapter 2A.

In operation, tap water passes from the conventional tube set 4, through both the tap water conduit 57 in the handpiece adapter 2A and the tap water tube-out 58, and to the water filter 55. The water filter 55 removes any impurities or contamination from the tap water and delivers filtered water to the filtered water conduit 59 in the handpiece adapter 2A via the filtered water tube-in 60.

While the invention has been primarily described as a sterile water delivery system, the apparatus may of course be used to deliver other fluids by themselves or with water. For example, it may be desirable to deliver medications or antiseptics with water.

While the above detailed description has shown, described, and pointed out the fundamental novel features of the invention as applied to two embodiments, it will be understood that various omissions, substitutions, or changes in the form and details of the illustrated device may be made by those skilled in the art without departing from the spirit of the invention. Consequently, the scope of the invention should not be limited to the foregoing discussion but should be defined by the appended claims.

What is claimed is:

1. A sterile fluid delivery system, comprising:
   an adapter for connecting between a medical handpiece and a conventional tube set, said adapter including a sterile fluid inlet, a sterile fluid outlet for connecting to a fluid inlet in the handpiece, an inlet air conduit for ducting pressurized air from the conventional tube set to the handpiece for driving a motor in the handpiece, an exhaust air conduit for ducting air from the motor in the handpiece to the conventional tube set, and a pressure sensing outlet open to one of the air conduits in said adapter;

a pump having a fluid inlet for connecting to a sterile fluid supply, a fluid outlet for connecting to said adapter, and a control signal fitting for connecting to said adapter;

a sterile fluid supply tube for connecting the sterile fluid inlet of said adapter to the fluid outlet of said pump;

a control tube for connecting the pressure sensing outlet of said adapter to the control signal fitting of said pump; and a pressure sensitive switch connected to said control tube and to said control signal fitting of said pump, said switch activating said pump when said control tube is pressurized and deactivating said pump when said control tube is not pressurized.

2. The system of claim 1, wherein said pump comprises a peristaltic pump.

3. The system of claim 1, wherein said adapter has no tap water inlet and thus blocks off a tap water conduit in the conventional tube set.

4. The system of claim 1, further comprising a container for sterile fluid and a supply tube connecting said container to the fluid inlet of said pump.

5. The system of claim 1, including said handpiece, which is a dental handpiece.

6. The system of claim 5, further comprising a dental tool operably mounted on said dental handpiece.

7. The system of claim 1, wherein said handpiece is a dental scaler.

8. The system of claim 7, including a scaler tool operably mounted on said scaler handpiece.

9. The system of claim 1, wherein said handpiece is an endodontic handpiece.

10. The sterile water delivery system of claim 9, including an endodontic tool operably mounted on said endodontic handpiece.

11. The system of claim 1, wherein said pressure sensing outlet is open to the air exhaust conduit.

12. The system of claim 1, wherein said adapter includes a blocking wall which aligns with a tap water conduit of a conventional robe set when the adapter is connected to the tube set so that tap water does not enter the adapter.

13. The system of claim 1, including a conventional tube set having a connector at its forward end for connection to the adapter and has the capability to be connected to one or more air supplies and a community water supply, said adapter being constructed to block the community water supply in the tube set.

14. A handpiece adapter for a sterile fluid delivery system, comprising:

a body for connecting between a medical handpiece and a conventional tube set;

a sterile fluid inlet in said body;

a sterile fluid outlet in said body for connecting to a fluid inlet in the medical handpiece;

an inlet air conduit in said body for ducting pressurized air from the tube set to the handpiece;

an exhaust air conduit in said body for ducting air from the handpiece to the tube set; and a pressure sensing outlet in said body open to an air conduit in said adapter.

15. The handpiece adapter of claim 14, wherein said adapter body is closed in the area that mates with a tap water conduit in the tube set.

16. The adapter of claim 14, wherein said pressure sensing outlet is open to said exhaust air conduit.

17. A filtered water delivery system, comprising:

an adapter for connecting between a medical handpiece and a conventional tube set;

a tap water inlet in said adapter for receiving tap water from a conventional tube set;

a tap water outlet in said adapter containing a tap water tube-out for connecting to a water filter;

a filtered water inlet in said adapter containing a filtered water tube-in for connecting to the water filter; and a filtered water outlet in said adapter for connecting to a water inlet in a handpiece.

18. The system of claim 17, including a water filter connected to said tap water outlet and said filtered water inlet for filtering the tap water.

19. The system of claim 17, wherein said adapter has an inlet air conduit for ducting pressurized air from the tube set to the handpiece for driving a motor in the handpiece.

20. The system of claim 19, wherein said adapter has an exhaust air conduit for ducting air from the motor in the handpiece to the tube set.

21. A method for delivering sterile fluid to a medical handpiece, comprising the steps of:

supplying sterile fluid to a pump;

pumping the sterile fluid to a handpiece adapter;

delivering the sterile fluid from the handpiece adapter to the handpiece;

ducting pressurized air from a conventional tube set, through an inlet air conduit, and to the handpiece for driving a motor in the handpiece;

ducting exhaust air from the motor in the handpiece, through an exhaust air conduit to the conventional tube set;

sensing the pressure of the air in one of air conduits; and activating the pump in response to the sensed pressure and deactivating the pump in the absence of pressurized air in said one air conduit.

22. The method of claim 21, wherein said one air conduit is said exhaust air conduit.

23. The method of claim 21, including blocking in the adapter a tap water conduit in the conventional tube set.

24. A method for delivering filtered water to a medical handpiece, comprising the steps of:

receiving tap water from a conventional tube set by a handpiece adapter;

directing the tap water from the handpiece adapter to an external water filter;

filtering the tap water through the water filter;

directing the filtered water to the handpiece adapter; and delivering the filtered water from the handpiece adapter to the handpiece.

25. The method of claim 24, including ducting pressurized air from a conventional tube set, through an inlet air conduit in the adapter, and to the handpiece for driving a motor in the handpiece.

26. The method of claim 25, further comprising ducting exhaust air from the motor through an exhaust air conduit in the adapter to the conventional tube set.

* * * * *